US012768842B2

(12) United States Patent
Harding et al.

(10) Patent No.: US 12,768,842 B2
(45) Date of Patent: Oct. 20, 2026

(54) MASS SPECTROMETRY CONTROLS

(71) Applicant: THE BINDING SITE GROUP LIMITED, Birmingham (GB)

(72) Inventors: Stephen Harding, Birmingham (GB); Gregg Wallis, Birmingham (GB)

(73) Assignee: THE BINDING SITE GROUP LIMITED, Birmingham (GB)

( * ) Notice: Subject to any disclaimer, the term of this patent is extended or adjusted under 35 U.S.C. 154(b) by 1011 days.

(21) Appl. No.: 17/924,880

(22) PCT Filed: May 12, 2021

(86) PCT No.: PCT/GB2021/051136

§ 371 (c)(1),
(2) Date: Nov. 11, 2022

(87) PCT Pub. No.: WO2021/229220

PCT Pub. Date: Nov. 18, 2021

(65) Prior Publication Data

US 2023/0184782 A1 Jun. 15, 2023

(30) Foreign Application Priority Data

May 13, 2020 (GB) ..................................... 2007047

(51) Int. Cl.
*G01N 33/68* (2006.01)
*G01N 33/537* (2006.01)

(52) U.S. Cl.
CPC ..... *G01N 33/6854* (2013.01); *G01N 33/5375* (2013.01); *G01N 33/6851* (2013.01); *G01N 2458/15* (2013.01)

(58) Field of Classification Search
None
See application file for complete search history.

(56) References Cited

U.S. PATENT DOCUMENTS 8,933,396 B2 * 1/2015 Louette .............. G01N 30/8665 436/175
2019/0094239 A1 3/2019 Murray et al.

FOREIGN PATENT DOCUMENTS

CN 108885218 A 11/2018
EP 3196646 A1 7/2017
(Continued)

OTHER PUBLICATIONS

Li et al. Application of microfluidic devices to proteomics research: identification of trace-level protein digests and affinity capture of target peptides. Mol Cell Proteomics. Feb. 2002;1(2):157-68 (Year: 2002).*

(Continued)

*Primary Examiner* — Rebecca M Giere
*Assistant Examiner* — Alexander Alexandrovic Volkov
(74) *Attorney, Agent, or Firm* — Stites & Harbison PLLC; Mandala Wilson Decker

(57) ABSTRACT

The Invention provides a method of immunopurifying and characterising an analyte from a sample comprising: (i) providing a predetermined amount of a control substance bound to a substrate via a linkage cleavable by acidic pH and/or reducing agents and optionally additional analyte specific antibodies or fragments thereof bound to a substrate, wherein the control substance is specific for the analyte or is not specific for the analyte; (ii) allowing analyte when present in the sample to bind to the control substance or said optional additional analyte-specific antibodies or fragments, wherein the control substance bound to the substrate (i) may be provided after contacting the analyte with the optional additional analyte-specific antibodies (ii); (iii) washing unbound material away from the substrate; (iv) acid eluting the analyte bound thereto, from at least one substrate; (v) performing mass spectrometry to identify two or more peaks, at least one peak of which is associated with the (Continued)

presence of the analyte and at least a second peak which is associated with at least a portion of the control substance; and (vi) comparing the size or intensity of the second peak to a predetermined calibration value to allow the first peak associated with the analyte to be calibrated.

22 Claims, 15 Drawing Sheets

(56) References Cited

FOREIGN PATENT DOCUMENTS

| | | | |
|---|---|---|---|
| WO | 2014/134561 | A2 | 9/2014 |
| WO | 2017/144900 | A1 | 8/2017 |
| WO | 2019/195166 | A1 | 10/2019 |

OTHER PUBLICATIONS

Lu et al. Absolute quantification of specific proteins in complex mixtures using visible isotope-coded affinity tags. Anal Chem. Jul. 15, 2004;76(14):4104-11. (Year: 2004).*

Faria et al. Comparison of a stable isotope labeled (SIL) peptide and an extended SIL peptide as internal standards to track digestion variability of an unstable signature peptide during quantification of a cancer biomarker. J Chromatogr B Analyt Technol Biomed Life Sci. Sep. 15, 2015;1001:156-68 (Year: 2015).*

State Intellectual Property Office, Office Action (First Office Opinion Notice) issued in corresponding Application No. 202180039452.9 published Mar. 7, 2025.

United Kingdom Intellectual Property Office, Search Report issued in corresponding Application No. GB1813736.4, dated Mar. 27, 2019.

The International Bureau of WIPO, International Preliminary Report on Patentability issued in corresponding Application No. PCT/GB2021/051136, issued Nov. 15, 2022.

Sharpley, F.A., et al. “A novel mass spectrometry method to identify the serum monoclonal light chain component in systemic light chain amyloidosis.” Blood Cancer Journal (2019) 9:16.

Sepiashvili, L., et al. “Direct Detection of Monoclonal Free Light Chains in Serum by Use of Immunoenrichment-Coupled MALDI-TOF Mass Spectrometry.” Clinical Chemistry (2019) 65:8, pp. 1015-1022.

Li, H., et al. Chemical ligation and cleavage on solid support facilitate recombinant peptide purification. Protein Expression and Purification 50 (2006) 238-246.

European Patent Office, Examination Report issued in corresponding Application No. 21 731 557.1 dated Jan. 2, 2026.

Korean Intellectual Property Office, Office Action (Notice of Submission of Opinion) issued in corresponding Application No. 10-2022-7043530 mailed Jun. 29, 2026.

Murray, D., et al. “Detection and prevalence of monoclonal gammopathy of undetermined significance: a study utilizing mass spectrometry-based monoclonal immunoglobulin rapid accurate mass measurement.” Blood Cancer Journal (2019)9:102.

Li, H., et al. “General LC-MS/MS Method Approach to Quantify Therapeutic Monoclonal Antibodies Using a Common Whole Antibody Internal Standard with Application to Preclinical Studies.” Anal. Chem. 2012, 84, 1267-1273.

Heudi, O., et al. “Towards Absolute Quantification of Therapeutic Monoclonal Antibody in Serum by LC-MS/MS Using Isotope-Labeled Antibody Standard and Protein Cleavage Isotope Dilution Mass Spectrometry.” Anal. Chem. 2008, 80, 4200-4207.

* cited by examiner

Mass Spec IRS (Internal Reference Standards)

| Slide 1 | Sheep monoclonal antibody with a 'light' light chain (specificity for target, kappa, lambda or similar sized protein e.g. β2M). |
|---|---|
| | No Patient Sample |
| Start (Add a known concentration antibody/bead preparation) | 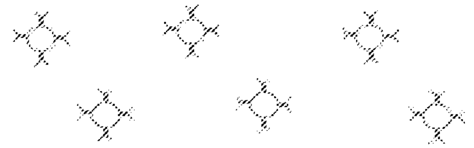 |
| Incubation (No binding) | 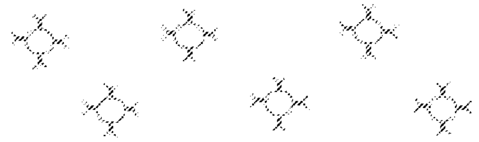 |
| Elution (Acid Reduction) followed by empirical quantification by LC-MS (liquid chromatography–mass spectrometry) |  |
| Mass Spectra on MALDI-TOF (light light chain is a known concentration) | 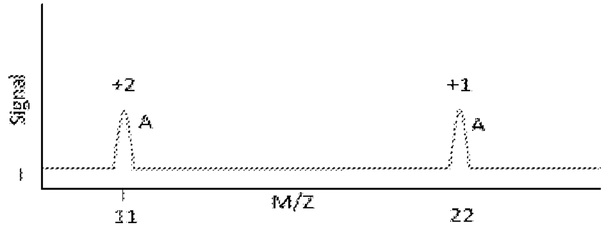  |

Key:  Sheep Mab Light Light Chain  Light Light Chain from Sheep Mab

Figure 1

Mass Spec IRS (Internal Reference Standards)

| **Slide 3** | Sheep monoclonal antibody with a 'light' light chain (specificity for target, kappa or lambda) with patient sample. |
|---|---|
| | With Patient sample |
| Start (known concentration of antibody/bead preparation including known amount of modified sheep light chain) | 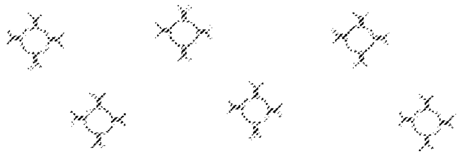 |
| Incubation with patient sample | 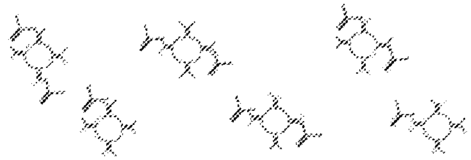 |
| Elution (Acid Reduction) |  |
| Mass Spectra on MALDI-TOF (light light chain is a known concentration (A) and can be used to quantify patient light chain (C)) | 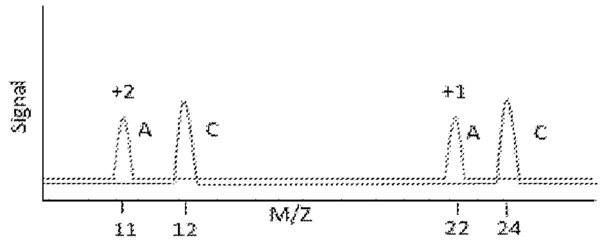  |

Key: Sheep Mab Light Light Chain; Patient/Human Antibody; Light Light Chain from Sheep Mab; Light Chain from Human Antibody

Figure 3

MASS SPECTROMETRY CONTROLS

The invention relates to methods of immunopurifying and characterising analytes and to kits for use in such methods.

The use of mass spectrometry in in-vitro diagnostics for the quantification of analytes, such as proteins, including immunoglobulins, is generally known in the art. For example, WO 2015/154052, incorporated herein in its entirety, discloses methods of detecting immunoglobulin light chains, immunoglobulin heavy chains, or mixtures thereof using mass spectrometry (MS). Samples comprising immunoglobulin light chains, heavy chains or mixtures are immunopurified and subjected to mass spectrometry to obtain a mass spectrum of the sample. This can be used, for example, to detect monoclonal proteins in samples from patients. It can also be used to fingerprint, isotype and identify disulphide bonds in monoclonal antibodies.

MS is used to separate, for example, lambda and kappa chains in the sample by mass and charge. It may also be used to detect the heavy chain component of immunoglobulins following, for example, reducing the disulphide bonds between heavy and light chains using a reducing agent. MS is also described in, for example, WO 2015/131169, herein incorporated in its entirety.

The purification of analytes in a sample typically uses anti-analyte specific antibodies. These are typically bound by techniques generally known in the art to a substrate, such as nano or micro beads. The sample containing the analyte is mixed or incubated with the antibodies attached to the beads, the analyte binds to the antibodies, and unbound material is washed away. The analyte is then washed off or detached or eluted from the beads and analysed by mass spectrometry. One problem associated with mass spectrometry in in-vitro diagnostics for the quantification of, for example serum proteins, is that it presents challenges with respect to the precision and accuracy of the reported results.

Solutions to date include, for example, the use of controls at individual specific steps in the procedure. For example, in MALDI-TOF, controls may be included in the matrix at the point of preparing the target, thus controlling for the crystallisation process and subsequent ionisation by the laser. However, this will not account for variability introduced upstream of this. In many of the pre-acquisition purification techniques used in mass spectrometry, the analyte is purified by immunoprecipitation. This requires controls to be used at each step of the purification process with known amounts of target protein to estimate the amount of analyte lost at each step of the process. However, this does not control for example variations in the precipitation of the sample and onward preparation steps, for example due to pipetting errors.

The Applicants have realised that using releasable control substances, such as protein or peptide, a heteropolymer, or antibody, bound to the beads or other substrate, such as a solid surface, that are precipitated in the purification or enrichment step would ensure that the releasable control substance could be used as a control within the purification process, through to the detection step by mass spectrometry. As the amount on the bead will be known, this can then be used to control for any losses in this step or variations in subsequent steps. As the control is, for example, from the antibody targeted to the analyte itself, there will be a direct relationship to the amount of control measured in the mass spectrometric spectra to the amount of target analyte measured in the same spectra. The amount of control in the precipitation/enrichment step is known, so a value can be assigned to the level of target analyte in the original sample.

For example a captive antibody specific for the analyte, or indeed another antibody may be bound to a substrate, such as bound via the constant region of the heavy chain when analyte bound to the captive antibody is eluted, for example via acid elution, light chains may be released from the captive antibody or other antibody and those light chains may be detected by mass spectrometry.

The ability to distinguish those light chains from, for example, light chains where immunoglobulins are the analyte, may be enhanced by selecting the light chains of the captive antibody or other antibody so that they are heavier or lighter than the light chains of the analyte. This may be achieved by, for example, selecting a monoclonal antibody and altering a light chain of the monoclonal antibody by adding one or more amino acids, especially 1 to 5 amino acids with the light chain.

The Applicant has recognised that other controls, such as heteropolymers where a detectable portion of subunit is released by, for example, acid elution may be used. For example, a non-immunoglobulin protein comprising one or more subunits may be used, where a subunit is released by the elution step.

This has the advantage that this controls for variation at each step of the elution and subsequent detection steps.

The invention provides a method of immunopurifying and characterising an analyte from a sample comprising:

(i) providing a predetermined amount of a control substance bound to a substrate via a linkage cleavable by acidic pH and/or reducing agents and optionally additional analyte specific antibodies or fragments thereof bound to a substrate, wherein the control substance is specific for the analyte or is not specific for the analyte;
(ii) allowing analyte when present in the sample to bind to the control substance or optional additional analyte-specific antibodies or fragments, wherein the control substance bound to the substrate may be provided after contacting the analyte with the optional additional analyte-specific antibodies;
(iii) washing unbound material away from the substrate;
(iv) acid eluting the analyte bound thereto, from at least one substrate;
(v) performing mass spectrometry to identify two or more peaks, at least one peak of which is associated with the presence of the analyte and at least a second peak which is associated with at least a portion of the control substance; and
(vi) comparing the size (such as area under the curve) or intensity of the second peak to a predetermined calibration value to allow the first peak associated with the analyte to be calibrated.

The control substance and optional analyte specific antibodies may be bound to the same substrate or different substrates. For example the control substance may be bound to a first group of beads and the additional analyte specific antibody many be bound to a second set of beads. Alternatively they may be bound to the same beads. The control substance may be an analyte-specific antibody or fragment thereof. Alternative the control may be, for example an antibody or fragment therefore which is not specific for the analyte. In the latter example, the optional additional analyte specific antibodies or fragments are typically provided to bind the analyte to the substrate, prior to the washing step.

At least a portion, but typically substantially all of the control substance is released from the substrate by the acid elution step.

One or more additional reducing agents, such as dithiothreitol (DTT) or Tris(2-carboxyethyl)phosphine hydrochloride (TCEP), may be included as appropriate (for example with disulphide linkages) to help reduce and break the cleavable linkage.

The control substance may potentially be any moiety which, when released can be detected by the mass spectrometry step. However, typically it is selected to have a similar mass and charge to the analyte being detected. Typically the mass and charge are different so that the peak from the control substance may be baseline discriminated from the peak of the analyte. The control substance may also be selected to crystalize in a similar manner to the analyte when placed (spotted) on a mass spectrometry target plate.

The analyte may, for example be an analogue of the analyte. This may be modified by altering the mass isotopically, or for example, increasing or decreasing the mass, for example, by addition or deletion of one or more amino acids where the analyte is a protein or peptide.

Where the analyte is an immunoglobulin light chain or heavy chain, the difference in mass of the control substance, such as a control light chain or heavy chain is at least 1000 Da to ensure that the MS peak(s) of the control is separated from the analyte peak(s).

The linkage may be cleaved by the acid in the acid elution. The linkages may also be reducing agent cleavable. Examples of linkages include disulphide bonds which are reduced by the acid and/or reducing agents to release the control substance.

The linkage may, for example, include a biotin molecule. One or other of the substrate or the control substance may be provided with one portion of the linkage, the other being present on the other part of the substrate-control substance complex. Maleimides may also be used to bind proteins or peptides to the substrate via reaction with sulfhydryl groups.

Other acid or reducing agent-cleavable bonds that have been used in, for example, acid-cleavable drug delivery systems, which may also be useful in the current system, include for example, orthoesters, acetals, hydrazones, imines, cis-aconytil, and trityl bonds (Binaud S. and Stenzel M. H. Chem Comm (2013), 49, 2082-2102).

The control substance is typically a polymeric macromolecule, such as a peptide or protein, but may potentially be any detectable compound, including nucleic acids, such as DNA or RNA.

The control substance may be a portion of a heteropolymer. This may potentially be any compound having two or more subunits, one of which is attached to the substrate and the second of which (acting as the control substance) is separable by the acid elution and is then detected as the second peak. Typically the second subunit is selected to have substantially the same ionisation characteristics as the analyte, and to typically have a similar, but not identical mass to the analyte being detected. Thus the second subunit is selected to produce one or more mass spectrometry peaks which do not substantially overlap with the mass spectrometry peak(s) of the analyte so that the first peak of the analyte and the second peak of the at least of portion of the heteropolymer can be distinguished and measured.

The heteropolymer is typically a protein. The subunits may be, for example, subunits attached via one or more disulphide bonds which may be broken by the acid elution step to release one or more of the subunits.

The heteropolymer may be an antibody or fragment of any antibody. It may comprise at least one heavy chain or fragment thereof and at least one light chain or fragment thereof, typically connected via one or more disulphide bonds.

The antibody or antibody fragments may themselves be analyte specific antibodies or fragments (such as $F(ab')_2$) or light chains a portion of which is then detected as the second peak. The optional additional analyte specific antibodies typically would not be used in that case.

Where antibodies or fragments are used the light chain may be modified by addition or deletion of one or more (e.g. up to 5) amino acid to the C-terminus to increase the mass of the light chain.

Antibodies or fragments may also be modified by the addition of chemical modifiers to increase the mass of the light chain. For example; N-Succinimidyl 3-(4-hydroxyphenyl)propionate and 6-Biotinamidohexanoic Acid N-Succinimidyl Ester, Biotin-PEG36-pentafluorophenyl-ester and NHS-PEG4-Biotin.

Kappa light chains have been found to be preferentially bound by some chemical modifiers, including those with biotin-PFP, on for example an IgG kappa and also preferentially compared to lambda light chains. The level of binding to the kappa light chains can be controlled. Lambda light chain modifications have also been observed by the Applicant.

The predetermined calibration value may be calculated by performing each of steps (i) to (v), without the presence of the analyte. That is, the predetermined amount of control substance bound to at least one substrate is not contacted with the antibodies or fragments, but is instead contacting with a control substance solution without the presence of the analyte, the washing steps and acid eluting steps (iii) and (iv) are carried out in the same way as described above. The amount of eluted control substance is then quantified. This may be, for example, by liquid chromatography-mass spectrometry (LC-MS).

The amount of antibody eluted may be used to determine a calibration value for that sample.

The calibration step may be carried out substantially at the same time as performing the purifying and characterising steps with the analyte. Alternatively, it may be carried out before, for example, supply of the analyte-specific antibodies bound to the substrate, at the supplier's laboratory. The calibration value may then be supplied with each batch of the analyte-specific antibodies bound to the substrate. That predetermined value provides a constant against which variations in the purification procedure with the analyte may be calculated.

The analyte may be, for example, a serum protein, such as an immunoglobulin or fragment thereof or other serum proteins such as albumins, clotting factor, regulatory proteins, beta 2-microglobulin, C-reactive protein, alpha-1 antitrypsin, alpha-1 fetoprotein etc.

Examples of antibodies include polyclonal and monoclonal antibodies, from sheep, cattle, horse, rat, mouse, rabbit, camelid or recombinant and synthetic antibodies.

The antibodies or fragments thereof may be intact antibodies or, for example, $F(ab')_2$ fragments.

The buffers associated with washing, acid elution, and performing the mass spectrometry are generally known in the art. Typically (but not exclusively) the pH of the acid eluting step is pH 7 or less than 7, typically less than 5 or more than 1.5, such as 2-3. Such buffers are typically compatible with mass spectrometry, such as MALDI-TOF, including:

The following shows buffers suitable for using with MALDI-TOF and for example peptides or proteins with typical maximum concentrations.

| Maximum Allowable Concentration (approx.) (*J. Chromat. A* 894 (2000) 345-355) | |
|---|---|
| Component | Maximum Concentration |
| Ammonium Acetate* | 500 mM |
| Ammonium Bicarbonate | 250 mM |
| CAPS | 200 mM |
| Dithiothreitol (Dtt) | 500 mM |
| EPPS | 250 mM |
| Glycerol | 1% v/v |
| Glycine | 500 mM |
| Guanidine-HCl | 500 mM |
| HEPES | 100 mM |
| Imidazole | 250 mM |
| MES | 100 mM |
| Sodium Acetate | 200 mM |
| Sodium Azide | <1 mM |
| Sodium Borate | 100 mM |
| Sodium Carbonate | 200 mM |
| Sodium Chloride | 100 mM |
| Sodium Citrate | 150 mM |
| Sodium Phosphate | 10 mM |
| Tris | 350 mM |
| Urea | 500 mM |

*when Amm. Acetate is used in conjunction with SDS or BRIJ 35 the max. concentration of these detergents can reach 30 mM. In any other buffer, Brij 35 and SDS are not typcally compatible with MALDI analysis and must be completely removed.

Detergents/Surfactant Tolerances for MALDI-TOF (Especially for Biological Samples: Peptides, Proteins)

| Category | Detergent | Critical Concentration | Type |
|---|---|---|---|
| C, D | Brij 35-97 | >0.01% v/v* | non-ionic |
| D | CHAPS | >0.01% v/v | zwitterionic |
| D | CHAPSO | >0.01% v/v | zwitterionic |
| A | n-Decyl-a-D-glucopyranoside | n/a | non-ionic |
| A | Octyl-B-D-glucopyranoside | 1.0% v/v | non-ionic |
| C | PEG- polyethylene glycol | 0.1% w/v | non-ionic |
| D | SDS | >0.01% w/v* | anionic |
| C, D | Tergitol NP-40 | >0.1% v/v | non-ionic |
| D | Thesit | n/a | non-ionic |
| C | Triton X-100, -100R, -114 | >0.1% v/v | non-ionic |
| C, D | Tween | >0.1% v/v | non-ionic |

CATEGORY A ACCEPTABLE
CATEGORY B NONE OR SMALL NEGATIVE EFFECT
CATEGORY C SIGNAL REDUCTION AND QUALITY AFFECTED
CATEGORY D TYPICALLY NOT COMPATIBLE WITH MALDI TOF

*when Amm. Acetate is used in conjunction with SDS or BRIJ 35 the max. concentration of these detergents can reach 30 mM. In any other buffer, Brij 35 and SDS are not typically compatible with MALDI analysis and must be completely removed.

Typically MALDI-TOF mass spectrometry is used to produce at least a peak for the analyte (where present) and the second peak associated with the at least a fragment of the control substance used in the purification steps.

The second peak is typically a light chain or fragment of a light chain of the antibody. Two or more peaks may be present where, for example, multiple charged antibody fragments or antibodies, are produced by the mass spectrometry process. The acid elution typically dissociates heavy chains from light chains of the antibodies.

Where a separate control substance is used and the analyte is an immunoglobulin, the analyte specific antibody may be crosslinked to prevent release of light chains bound to the heavy chains and so prevent interference of the sample with, for example, light chains released from the analyte specific antibody or fragment thereof.

Accordingly, the analyte specific antibody or fragment thereof may be crosslinked with, for example, a linkage which is stable under the acid elution correlations.

WO2006/099481A describes the use of intra- and inter-chain thioether cross links in a wide range of macromolecules including polypeptides such as polyclonal antibodies, monoclonal antibodies, Fab, F(ab) and $F(ab')_2$ fragments, single chain antibodies, human antibodies, harmonised or chimeric antibodies and epitope binding fragments. The document describes that the aim of the cross-linking is to enhance the stability and pharmaceutical and functional properties of the antibody or fragment. In particular, the aim is to cross-link, for example, the heavy and light chains of different monoclonal antibodies, such as anti-viral antigen antibodies, including anti-RSV antibodies. The stated aim is to improve the pharmaceutical properties of the antibodies.

WO00/44788 describes using thioethers to cross-link different antibody molecules of different specificities with the aim of producing improved therapeutic agents. Similarly, bi- or tri-specific $F(ab)_3$ or $F(ab)_4$ conjugates with different specificities are shown in WO91/03493.

Thioethers have been observed in therapeutic antibodies with increasing levels on storage (Zhang Q et al JBC manuscript (2013) M113.468367). A light chain-heavy chain disulphide (LC214-HC220) can convert to a thioether bond. One IgG1k therapeutic antibody was observed to convert to a thioether at that position at a rate of 0.1% per day whilst circulating in blood. Endogenous antibodies were also observed to be formed in healthy human subjects. Zhang et al repeated the thioether formation in vitro. This was used to help assess the safety impact of the thioether bonds on therapeutic monoclonal antibodies.

The cross-links are typically intramolecular between chains of the same antibody.

The cross-link typically comprises a thioether bond.

A thioether cross-link comprises a thioether bond. This is a link between residues of the antibody wherein the link has a single sulphur bond rather than a disulphate bond. That is thioether cross-links do not include links that comprise more than one sulphur atom, such as disulphide bridges that are familiar to those skilled in the art. Instead, a thioether cross-link comprises a single sulphur bond that bridges residues of a macromolecule. One or more additional non-sulphur atoms may additionally form the link.

The residues linked by thioether cross-links can be natural residues or non-natural residues. Formation of the thioether cross-link can result in a loss of atoms from the residues, as will be recognised by those skilled in the art. For example, formation of a thioether cross-link between side chains of two cysteine residues can result in loss of a sulphur atom and hydrogen atoms from the residues, yet the resulting thioether cross-link will be recognised as linking the cysteine residues by one skilled in the art.

Thioether cross-links can link any two residues of the antibody. One or more of the residues may be selected, for example, from cysteine, aspartic acid, glutamic acid, histidine methionine and tyrosine. Two of the residues may be selected from the group consisting of cysteine, aspartic acid, glutamic acid, histidine, methionine and tyrosine. More typically two of the residues are cysteine residues. Typically, only one thioether cross-link is between the heavy chain and the light chain. Alternatively, two, three or more thioether cross-links may be used. The heavy chain pair of the antibody, or a fragment thereof, may also be linked by one or more non-disulphide cross-links, such as thioether bonds.

Thioether cross-links are described in, for example, WO2006/099481, and Zhang et al (2013) J. Biol. Chem. vol 288(23), 16371-8 and Zhang & Flynn (2013) J. Biol. Chem, vol 288(43), 34325-35 incorporated herein by reference.

Phosphines and phosphites may be used. Here, 'Phosphine' refers to any compound containing at least one functional unit with the general formulae $R_3P$ (where P=phosphorous and R=any other atom). In phosphites, the R positions are occupied specifically by oxygen atoms. $R_3P$-containing compounds act as strong nucleophiles that can attack disulphide bonds. This can result in reduction of disulphides, however under some conditions, may also result in thioether bond formation.

Compounds Include:

Tris(dimethylamino)phosphine (CAS Number 1608-26-0)

Tris(diethylamino)phosphine (CAS Number 2283-11-6)

Trimethylphosphite (CAS Number 121-45-9)

Tributylphosphine (CAS Number 998-40-3)

References: Bernardes et al. (2008) *Angew. Chem. Int. Ed.,* vol 47, 2244-2247 incorporated herein by reference Cross-links may also comprise cross-linkers such as a maleimide cross-linker, which reacts with free thiols to cross-link to chains of the antibody molecule. This can be made to bind on one side of a thiol group and additionally on another moiety such as a lysine carboxyl group, as described in WO00/44788.

Bi-functional cross-linkers may be used comprising two reactive moieties linked together by a linker, especially a flexible linker. The linker may comprise one or more carbons covalently bound together in a chain, for example a substituted or non-substituted alkyl. The linker especially a C1-C10, most typically a C2-C6 or C3-C6 linker. The Applicants have found that C2-C6 containing cross linkers, such as, α,α'-Dibromo-m-xylene, BMOE (bismaleimidoethane) or BMB (bismaleimidobutane) particularly useful with relatively high levels of recovery of cross-linked protein.

The size of the antibody or fragment thereof may be preselected to produce one or more peaks by mass spectrometry which are separated by one or more of the peaks associated with the analyte. This may be, for example, by selecting the size of the antibodies or fragments or alternatively the charge of the antibodies or fragments.

Where MALDI-TOF mass spectrometry is used, the peak is typically the m/z intensity.

The amount of the control substance such as the initial antibody added to the system is known. The amount of antibody expected without using analyte is also known because of the calibration value. Therefore, the amount of antibody in the peak with the analyte may be corrected by the calibration value to take into account any loss of material or, for example, pipetting errors. The ratio of the m/z peak intensity between the target and the antibody can control, for example, sample loss, loss of the substrate, target capture, analyte elution, analyte spotting and ionisation.

The ability to accurately couple a known mass of the antibody onto a bead so that its subsequent elution and m/z peak intensity can be used to quantify (by comparison, to the target peak). This improves the precision and accuracy so that it can be used for routine clinical procedure.

The substrate is typically a bead, for example, a magnetic bead, a latex bead, a ceramic bead, polystyrene or other substrate.

Magnetic and paramagnetic beads are generally known in the art

The absorption of antibodies to substrates, such as beads, is also generally known in the art. Typically they are covalently bonded via amino, carboxy, epoxy, or thiol-activated groups may be used. Passive adsorption may also be used.

Where magnetic beads are used it is possible to mix the bead with the bound antibodies in a sample containing the analyte, and precipitate the beads using a magnet. The antibodies or fragments thereof may be monoclonal antibodies or polyclonal antibodies or a mixture thereof.

Typically the antibody or fragment is not enzymatically digested after purification of the analyte.

The analyte may be potentially any suitable analyte. Typically the analyte and immunoglobulin co-crystallise and ionise in substantially the same manner when applied to a mass spectrometry target.

The sample may be from a plant or animal such as a mammal or typically a human. It may be a sample of tissue or bodily fluid such as blood, serum, plasma, sweat, saliva, CSF or urine.

The analyte may be an immunoglobulin or fragment thereof. For example, the immunoglobulin or fragment may be a human IgG, IgA, IgM, lambda light chain or kappa light chain.

The analyte may be a human analyte.

Typically where the analyte is an immunoglobulin, the antibodies or fragments thereof are monoclonal antibodies or fragments thereof. This is because the size of the monoclonal antibody may be tailored, for example by selecting the size of the monoclonal antibody or alternatively adjusting the mass by deletion of a fragment of the antibody or addition of amino acids to the antibody, to ensure that the antibody, or fragment thereof, does not overlap with the target size, for example to m/z peak observed for the analyte.

Immunoglobulins are by their nature very variable. Accordingly, one potential problem with some monoclonal antibodies is that they may not detect all variants of the analyte, such as monoclonal antibodies. This may be improved by, for example, coating the substrate with a predetermined amount of the monoclonal antibody or fragment thereof, and additionally a plurality of additional analyte specific antibodies or fragments thereof which are, for example, polyclonal antibodies. This allows for example a broad specificity of analyte capture to be achieved, at the same time as providing the predetermined antibody or fragment with the known peak or m/z size. A ratio of, for example, 10-20% predetermined monoclonal antibody (or fragment) to 90-80% polyclonal antibody may be used.

The antibodies or fragments thereof may be heavy chain class-specific, light chain type-specific, free light chain-specific, or heavy chain class light chain type-specific.

The method may be used to detect or prognose a disease by detecting the presence of analyte, or for example the concentration of the analyte in a sample. The disease may be any disease where an analyte may be purified via using analyte specific antibodies. For example, a B-cell related disease or other immunoglobulin related disease. Other examples may include acute phase markers, liver disease, and lung cancer biomarkers There are a number of proliferative diseases associated with antibody producing cells.

In many such proliferative diseases a plasma cell proliferates to form a monoclonal tumour of identical plasma cells. This results in production of large amounts of identical immunoglobulins and is known as a monoclonal gammopathy.

Diseases such as myeloma and primary systemic amyloidosis (AL amyloidosis) account for approximately 1.5% and 0.3% respectively of cancer deaths in the United Kingdom. Multiple myeloma is the second-most common form of haematological malignancy after non-Hodgkin lymphoma. In Caucasian populations the incidence is approximately 40 per million per year. Conventionally, the diagnosis of multiple myeloma is based on the presence of excess monoclonal plasma cells in the bone marrow, monoclonal immunoglobulins in the serum or urine and related organ or tissue impairment such as hypercalcaemia, renal insufficiency, anaemia or bone lesions. Normal plasma cell content of the bone marrow is about 1%, while in multiple myeloma the content is typically greater than 10%, frequently greater than 30%, but may be over 90%.

AL amyloidosis is a protein conformation disorder characterised by the accumulation of monoclonal free light chain fragments as amyloid deposits. Typically, these patients present with heart or renal failure but peripheral nerves and other organs may also be involved.

There are a number of other diseases which can be identified by the presence of monoclonal immunoglobulins within the blood stream, or indeed urine, of a patient. These include plasmacytoma and extramedullary plasmacytoma, a plasma cell tumour that arises outside the bone marrow and can occur in any organ. When present, the monoclonal protein is typically IgA. Multiple solitary plasmacytomas may occur with or without evidence of multiple myeloma. Waldenström's macroglobulinaemia is a low-grade lymphoproliferative disorder that is associated with the production of monoclonal IgM. There are approximately 1,500 new cases per year in the USA and 300 in the UK. Serum IgM quantification is important for both diagnosis and monitoring. B-cell non-Hodgkin lymphomas cause approximately 2.6% of all cancer deaths in the UK and monoclonal immunoglobulins have been identified in the serum of about 10-15% of patients using standard electrophoresis methods. Initial reports indicate that monoclonal free light chains can be detected in the urine of 60-70% of patients. In B-cell chronic lymphocytic leukaemia monoclonal proteins have been identified by free light chain immunoassay.

Additionally, there are so-called MGUS conditions. These are monoclonal gammopathy of undetermined significance. This term denotes the unexpected presence of a monoclonal intact immunoglobulin in individuals who have no evidence of multiple myeloma, AL amyloidosis, Waldenström's macroglobulinaemia, etc. MGUS may be found in 1% of the population over 50 years, 3% over 70 years and up to 10% over 80 years of age. Most of these are IgG- or IgM-related, although more rarely IgA-related or bi-clonal. Although most people with MGUS die from unrelated diseases, MGUS may transform into malignant monoclonal gammopathies.

In at least some cases for the diseases highlighted above, the diseases present abnormal concentrations of monoclonal immunoglobulins or free light chains. Where a disease produces the abnormal replication of a plasma cell, this often results in the production of more immunoglobulins by that type of cell as that "monoclone" multiplies and appears in the blood.

Kits comprising at least one substrate comprising a predetermined amount of a plurality of controls substance and optionally analyte specific antibodies or fragments thereof for use in a method according to the invention, additionally comprise a predetermined calibration value for calibrating the analyte to be calibrated. That is the kit is provided in combination with a reference value, which may be in the form of a numerical value to be programmed into, for example, a computer or alternatively provided on an automated chip system for loading into a computer. Alternatively, this may be provided as a bar code or QR code for uploading onto an assay device. That calibration value may be determined as described above. In such kits, the Control substance antibodies or fragments thereof may be as defined above.

A further aspect of the invention provides a mass spectrometer having means to execute steps (v) and (vi) of the invention. A computer program comprising instructions to cause the mass spectrometer to perform steps (v) and (vi) of the invention is also provided.

Computer readable medium comprising instructions which when executed on one or more processors compares the size or area of the second peak obtained by the method of the invention, with a predetermined calibration value is also provided. That medium may also compare the ratio of, for example, the peak size or m/z value of the second peak with the analyte peak.

The substrates and methods of binding antibodies to the substrates and subsequent elution and detection of the analyte and control substance, such as heteropolymer, for example antibody peaks are generally known in the art. Polyclonal anti-immunoglobulin antibodies, such as anti-light chain, anti-free light chain, anti-heavy chain and anti-heavy chain class—light chain type antibodies are available from, for example, The Binding Site Group Limited, Birmingham, United Kingdom. Monoclonal anti heavy chain and anti light chain antibodies are known in the art.

The invention will now be described by way of example only with reference to the following figures.

FIG. 1 shows the principle of utilising an antibody attached to a bead, following by an acid elution and MALDI-TOF. In this example no antigen is present and the concentration of antibody eluted from the substrate is detected by chromatography-mass spectrometry and quantified. The mass spectra on MALDI-TOF of the light chain from the antibody is also shown.

FIG. 3 shows the example of using monoclonal antibody with light chain specificity to detect and quantify light chains from a sample.

Figure 4:
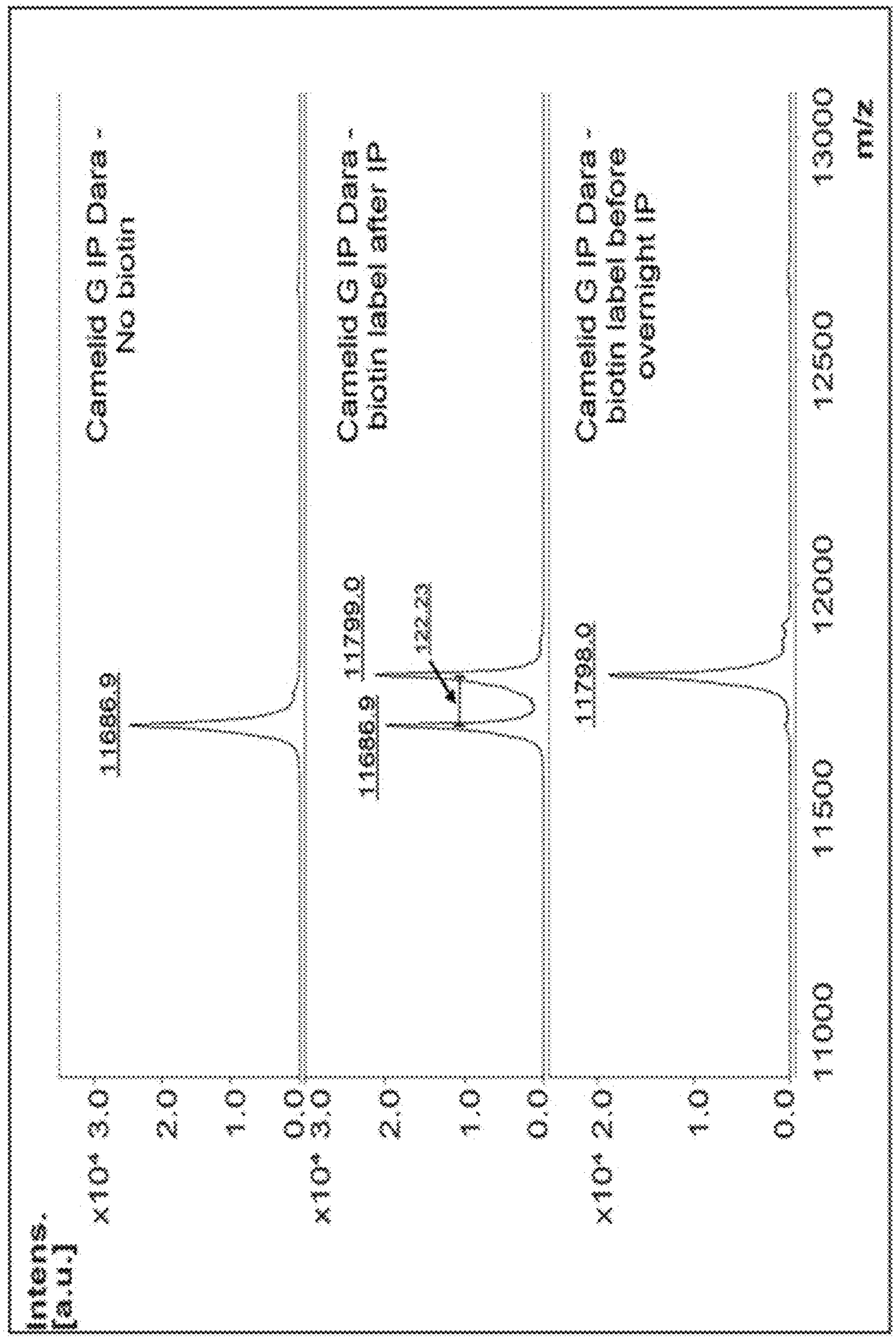

FIG. 4 Progressive biotinylation and mass-shifting of Daratumumab (an IgG Kappa CD38 specific monoclonal antibody) using PFP-Biotin.

Figure 5:
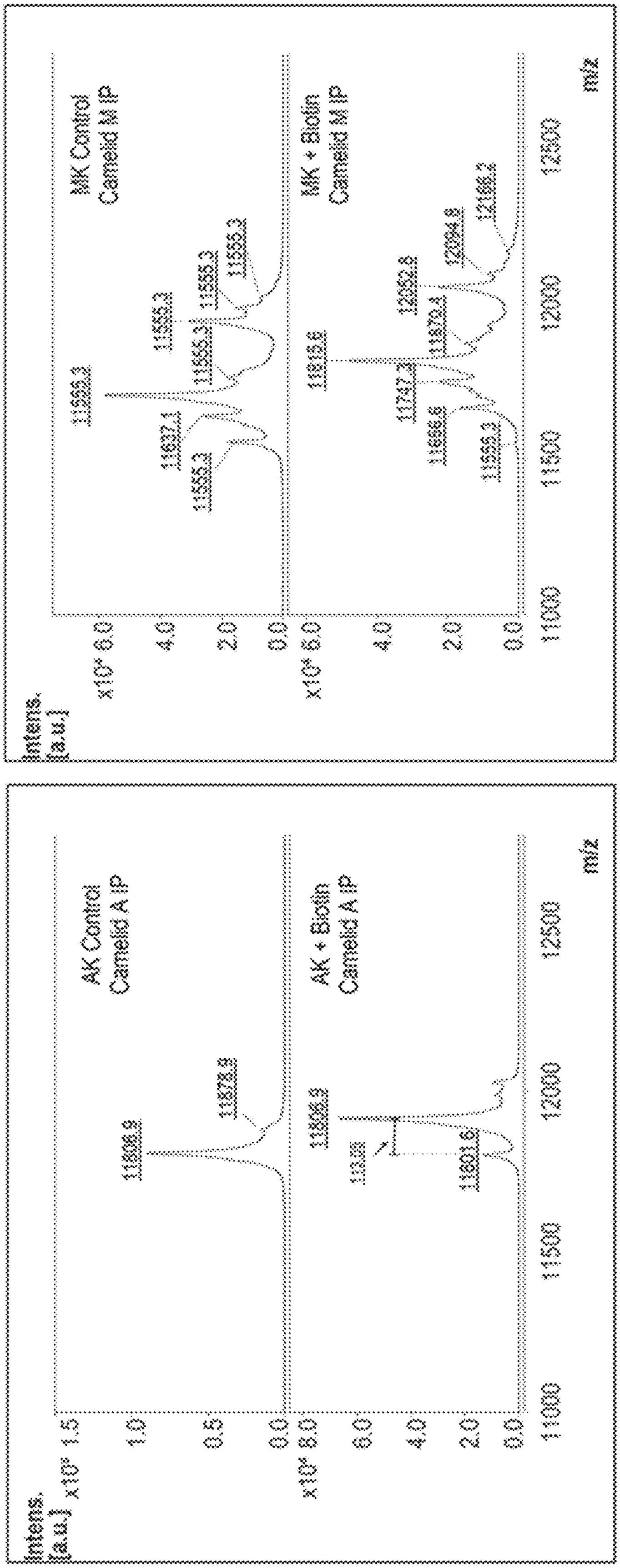

FIG. 5 Biotinylation and mass-shifting of polyclonal IgA (left panel) or polyclonal IgM (right panel) from healthy human serum.

Figure 6:
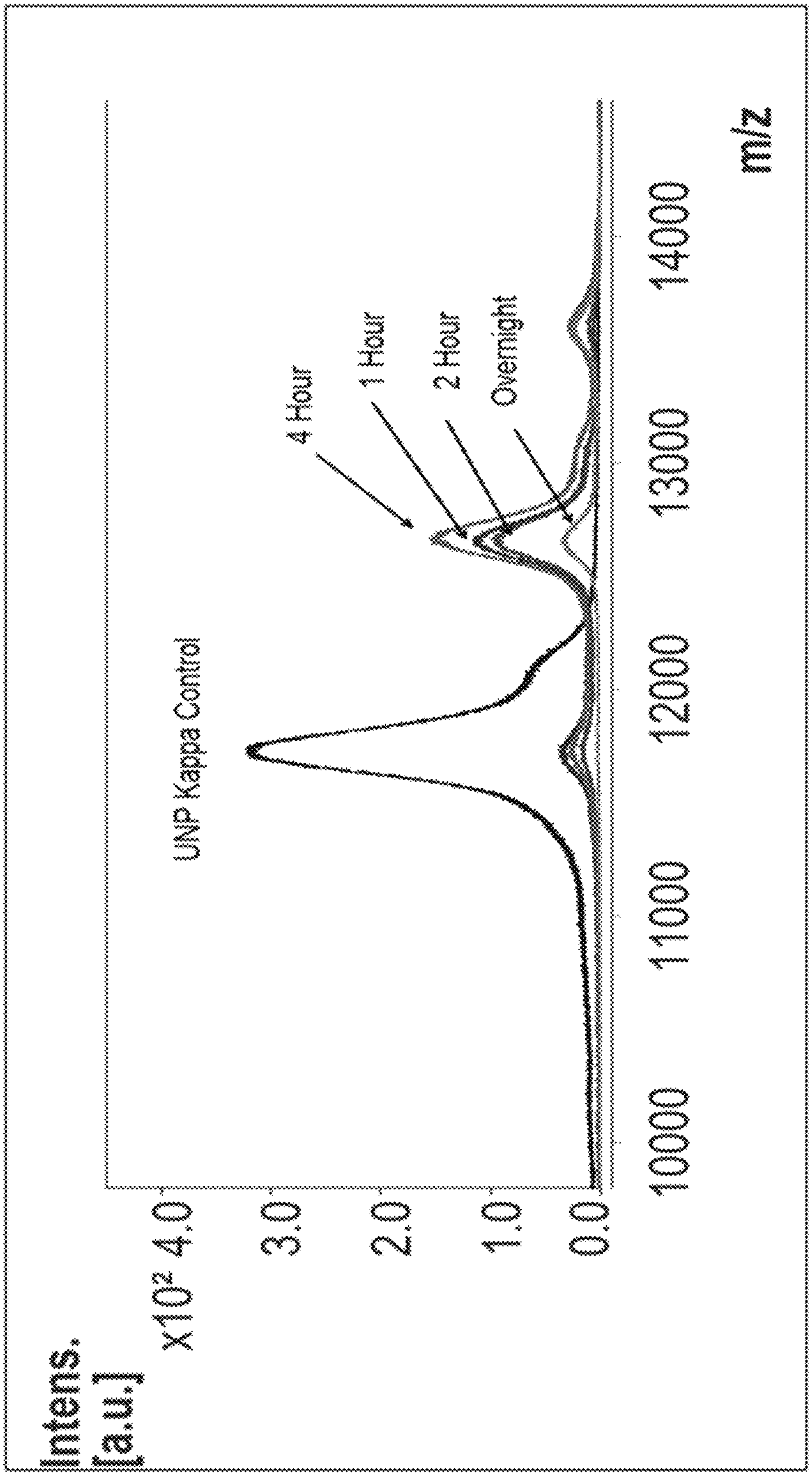

FIG. 6 Time course of biotinylation and mass-shifting of kappa light chains from polyclonal IgA and IgM using Biotin-PEG36-PFP.

Figure 7A:
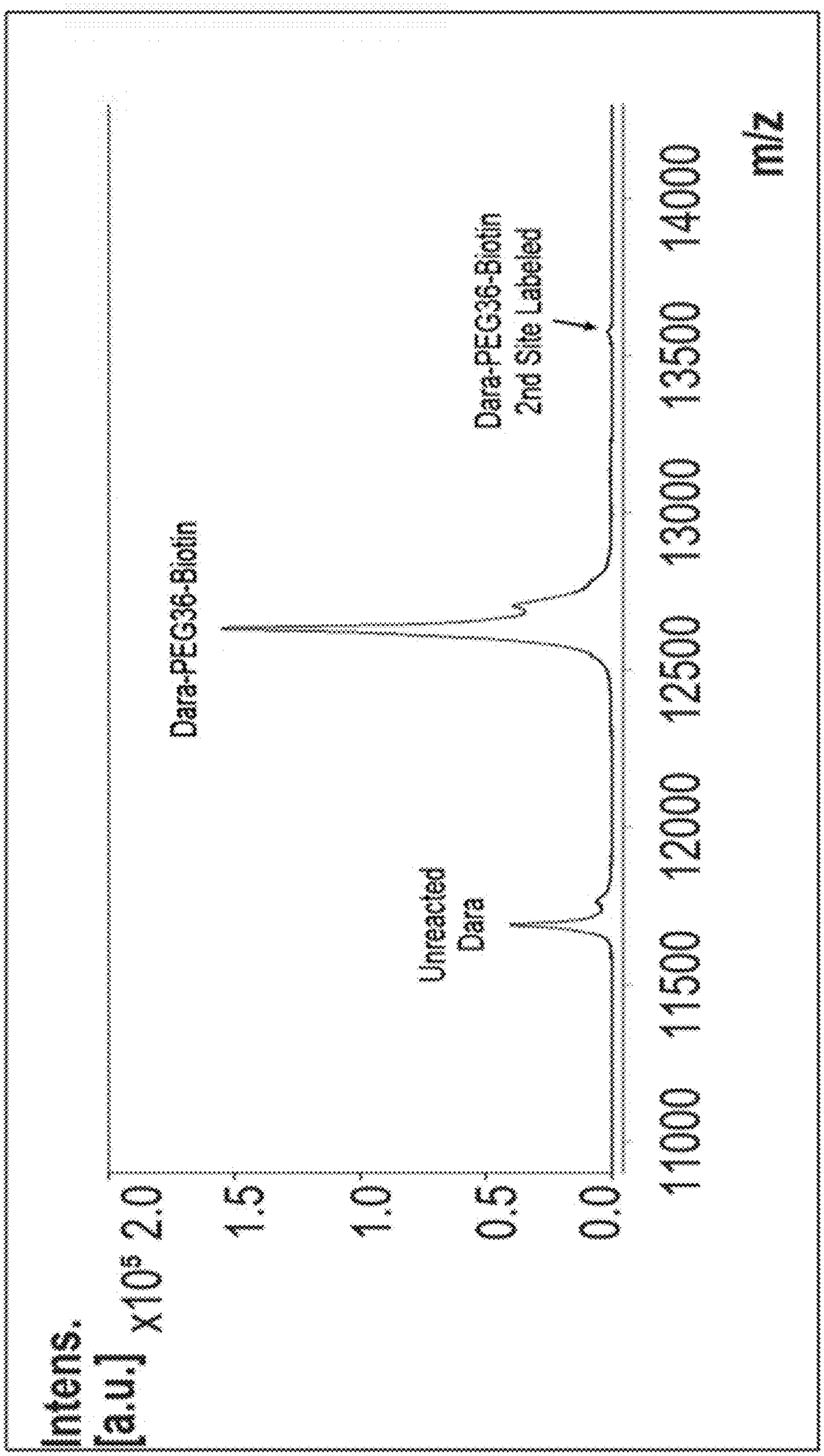
Figure 7B:
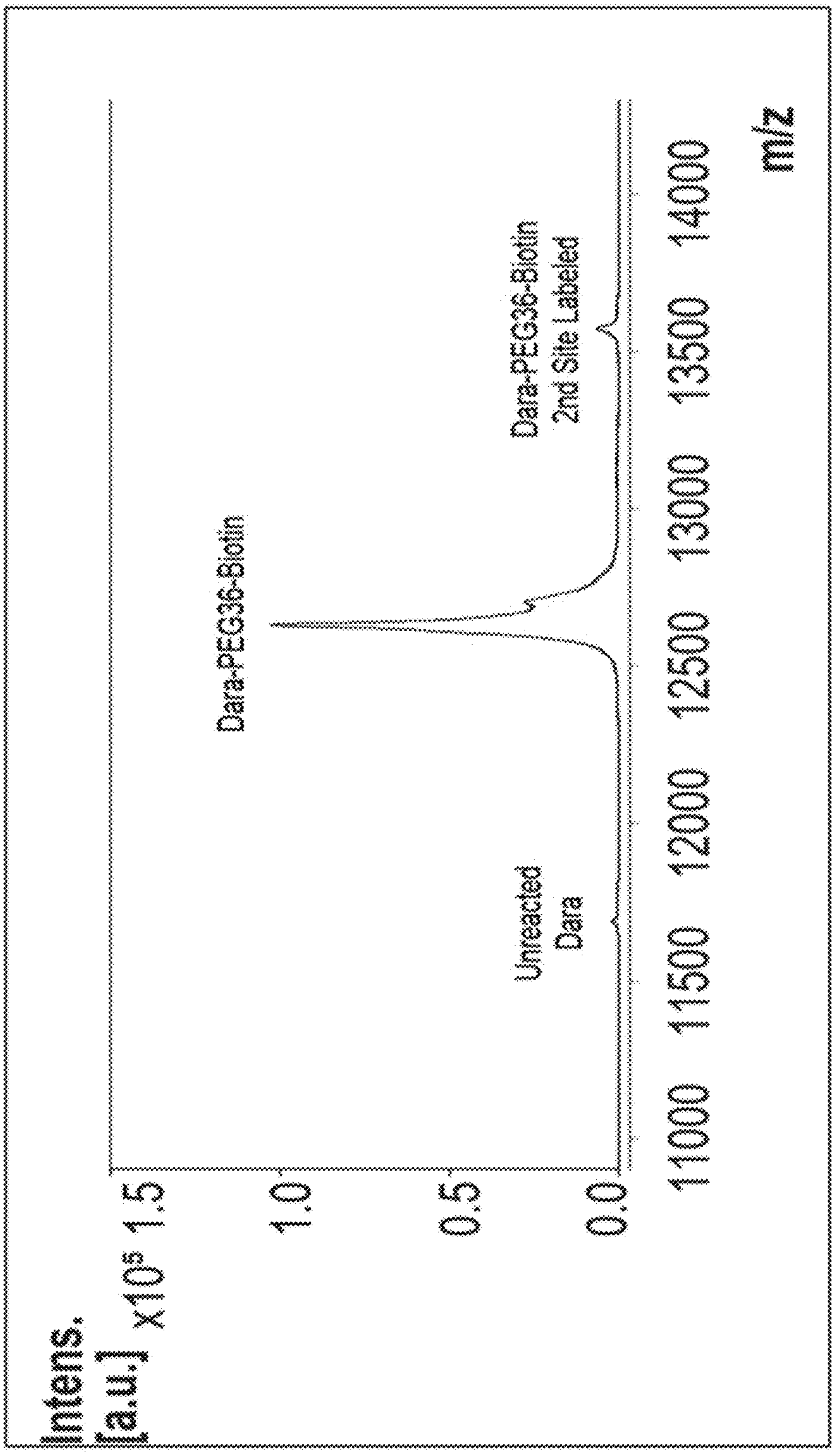

FIG. 7 Mass-modification of the Daratumumab kappa light chain using Biotin-PEG36-PFP. Labelling was performed for either 2 h using a single dose of the reagent (FIG. 7*a*) or 6 h with a second dose of the reagent added after 2 h (FIG. 7*b*).

Figure 8A:
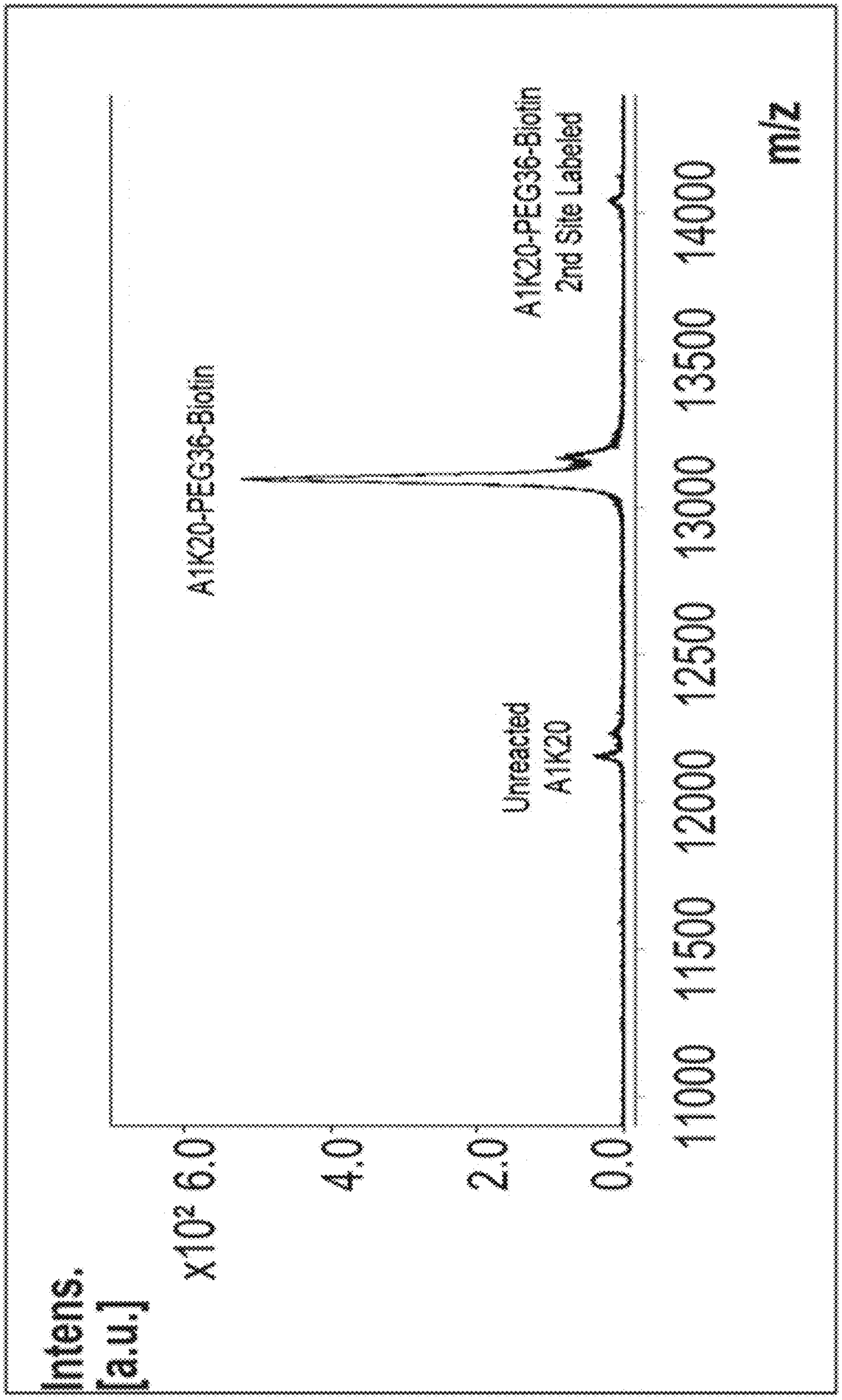
Figure 8B:
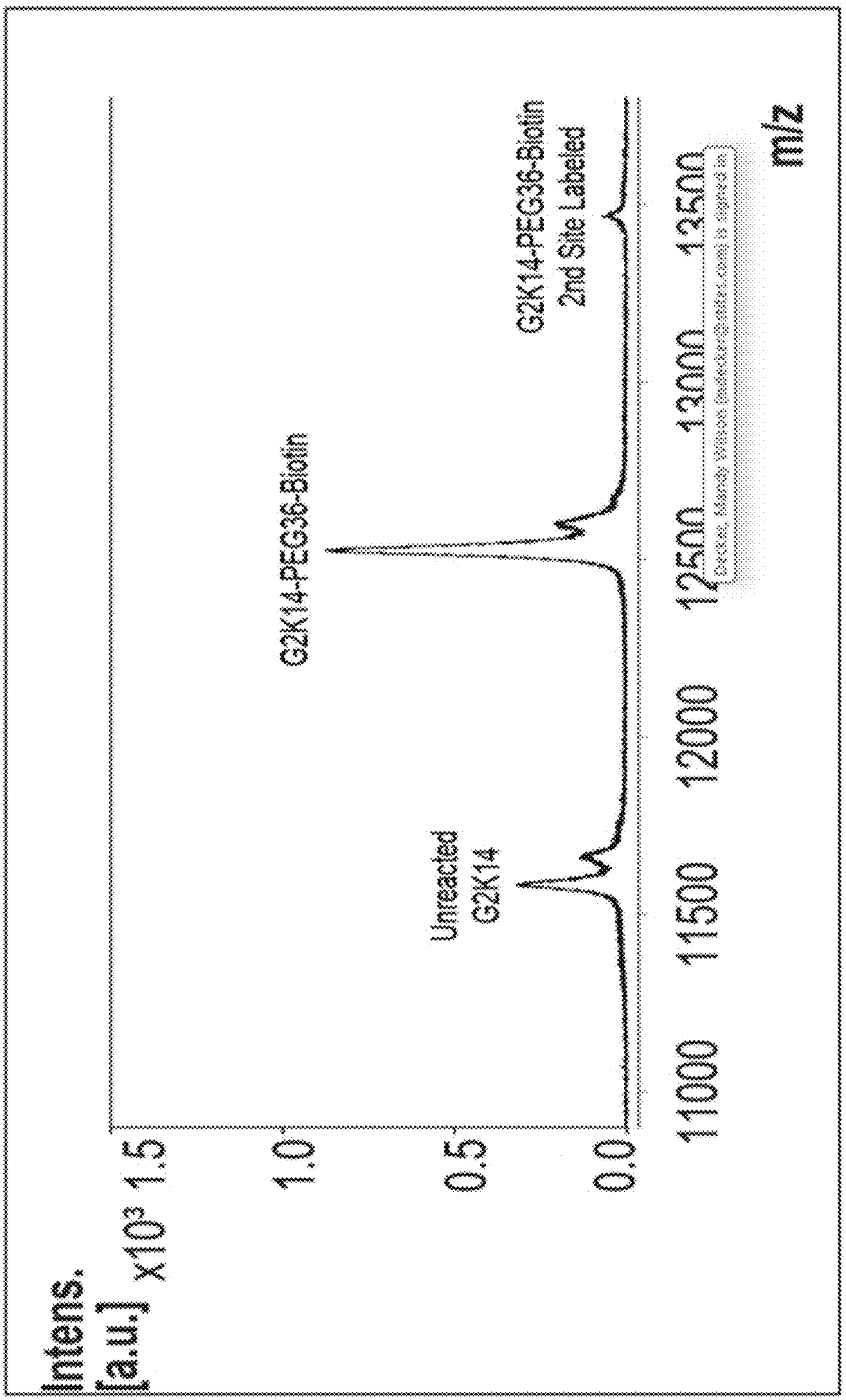

FIG. 8 Mass-modification and spectral shifting of monoclonal proteins. An IgAK (A1K20, FIG. 8*a*) and IgG2K (G2K14, FIG. 8*b*) were labelled using Biotin-PEG36-PFP.

Figure 9:
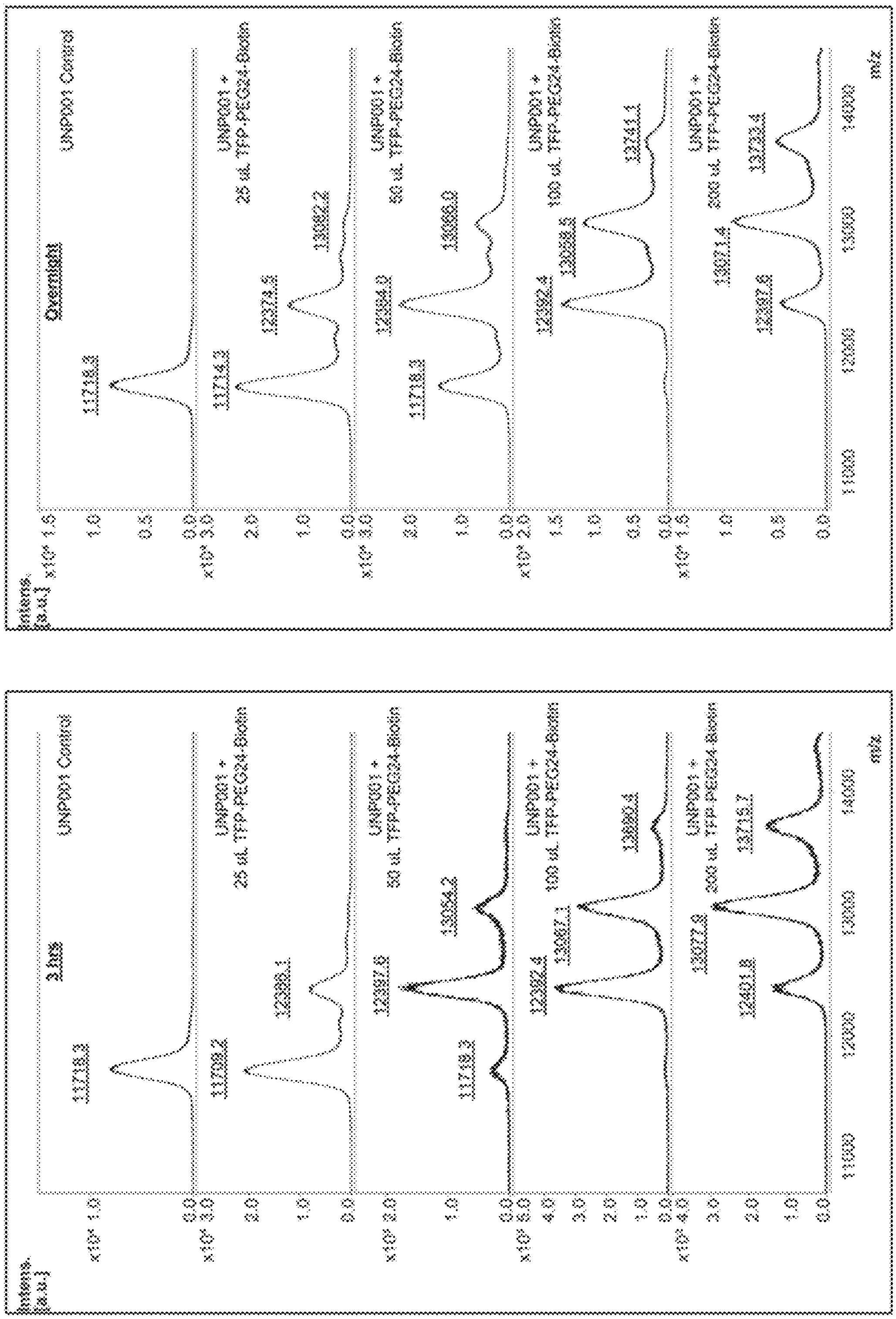

FIG. 9 Effect of increasing amounts of Biotin-PEG24-TFP and reaction time (3 h or overnight) on the mass-modification of polyclonal immunoglobulin kappa light chains in healthy serum.

Figure 10:
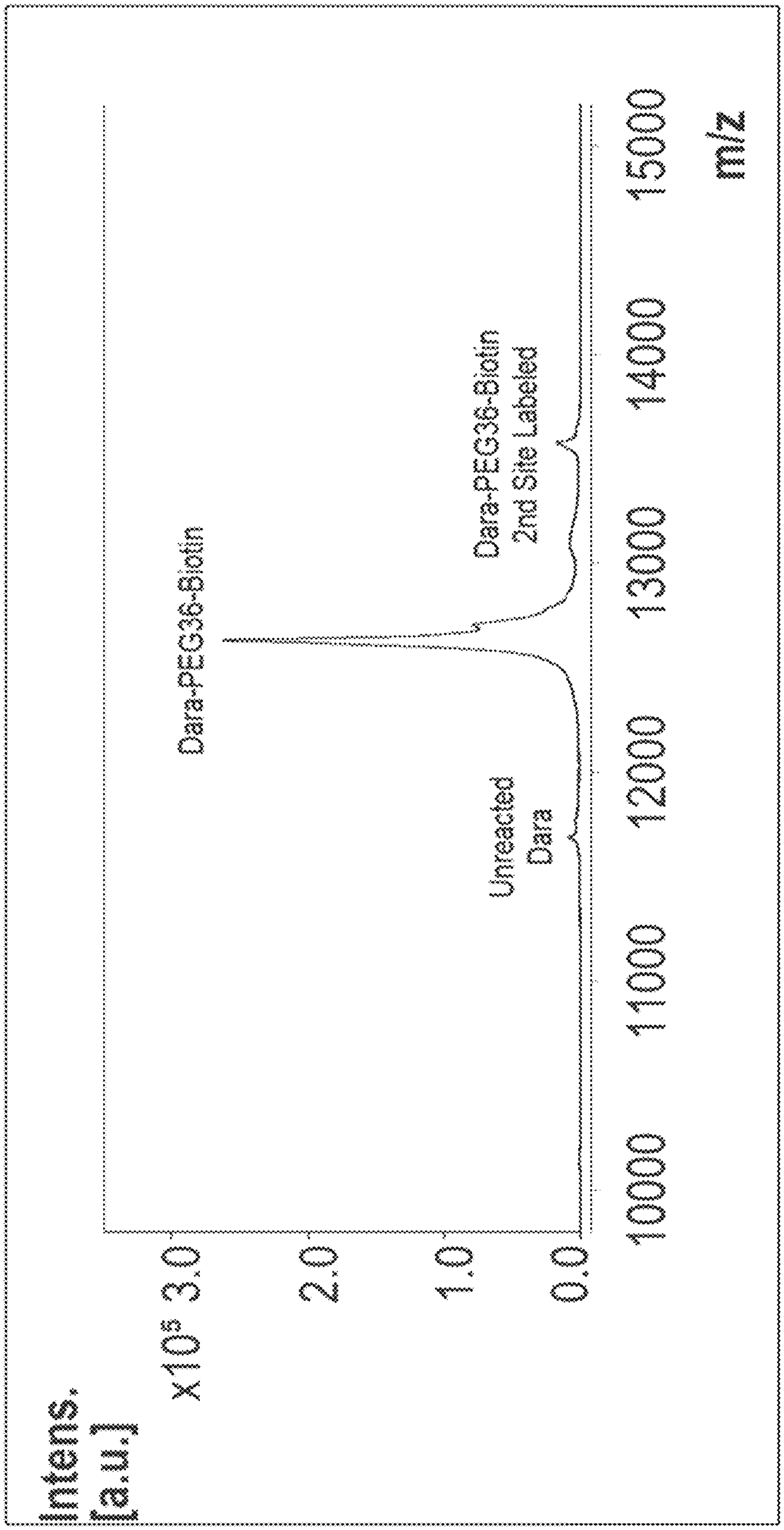

FIG. 10 Mass-modification of the Daratumumab kappa light chain using Biotin-PEG36-PFP, to use as a Mass std.

Figure 11:
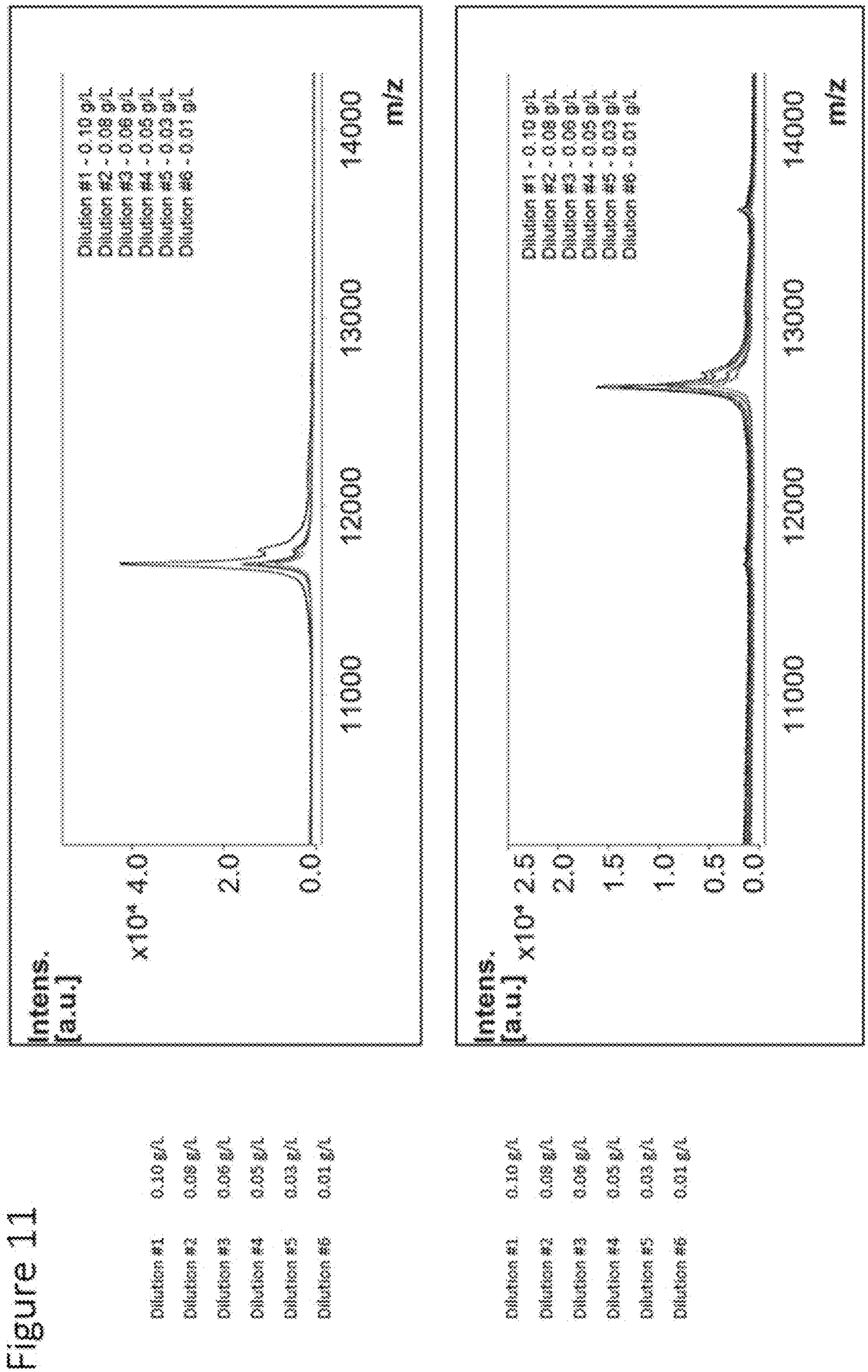

FIG. 11 Dose response data for MALDI-TOF signal intensity and Daratumumab concentration for mass-modified (lower panel) and unmodified (upper panel) kappa light chains.

Figure 12:
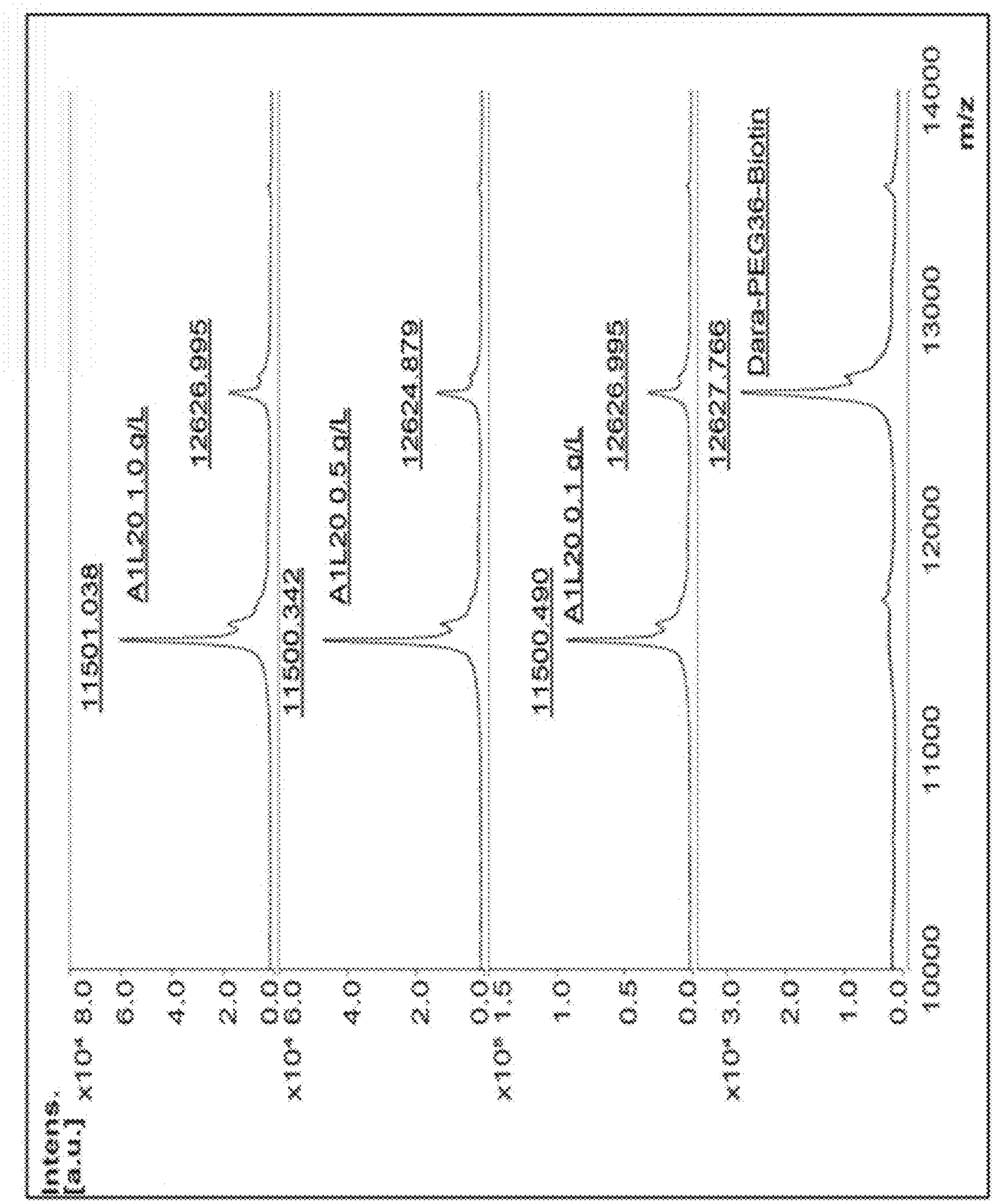

FIG. 12 Spiking of mass modified Daratumumab into the QIP-MS (immune-precipitation) reaction of a monoclonal IgAL (A1L20) clinical sample from a multiple myeloma patient.

Figure 13:
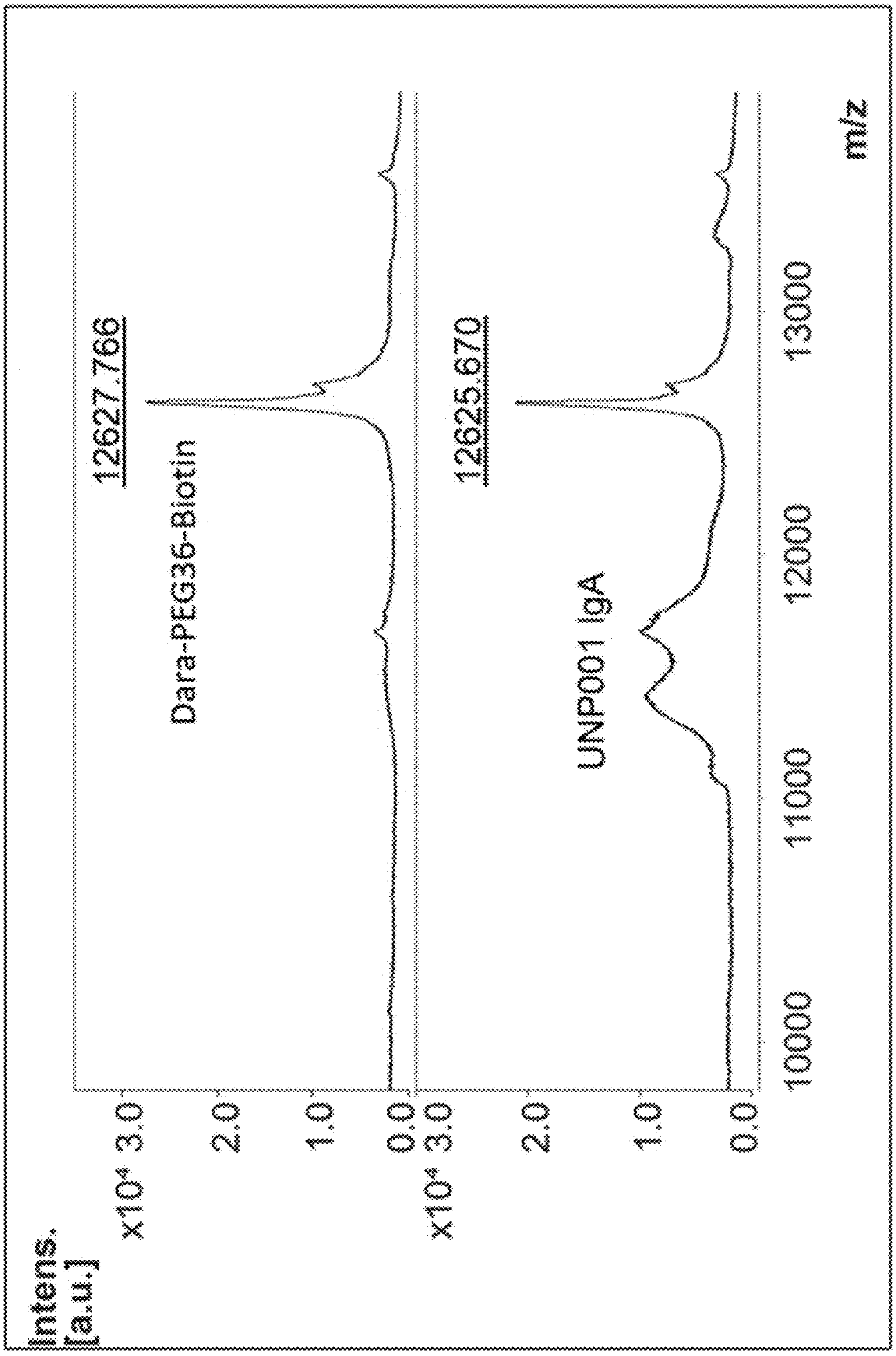

FIG. 13 Spiking of mass modified Daratumumab into the QIP-MS (immuno-precipitation) reaction of a healthy IgA (UNP001) clinical sample.

FIG. 1 is a schematic diagram showing, by way of example only, antibodies attached to a matrix, such as a bead. The antibodies may be attached by known techniques.

Where no analyte is present, or alternatively where this is used to produce a control calibration value, the antibody may be eluted by acid elution and the amount of antibody detected is quantified by LC-MS. A mass spectrometer produces, in this case, two peaks based on the charge and mass of the light chain from the eluted antibody.

Figure 2:
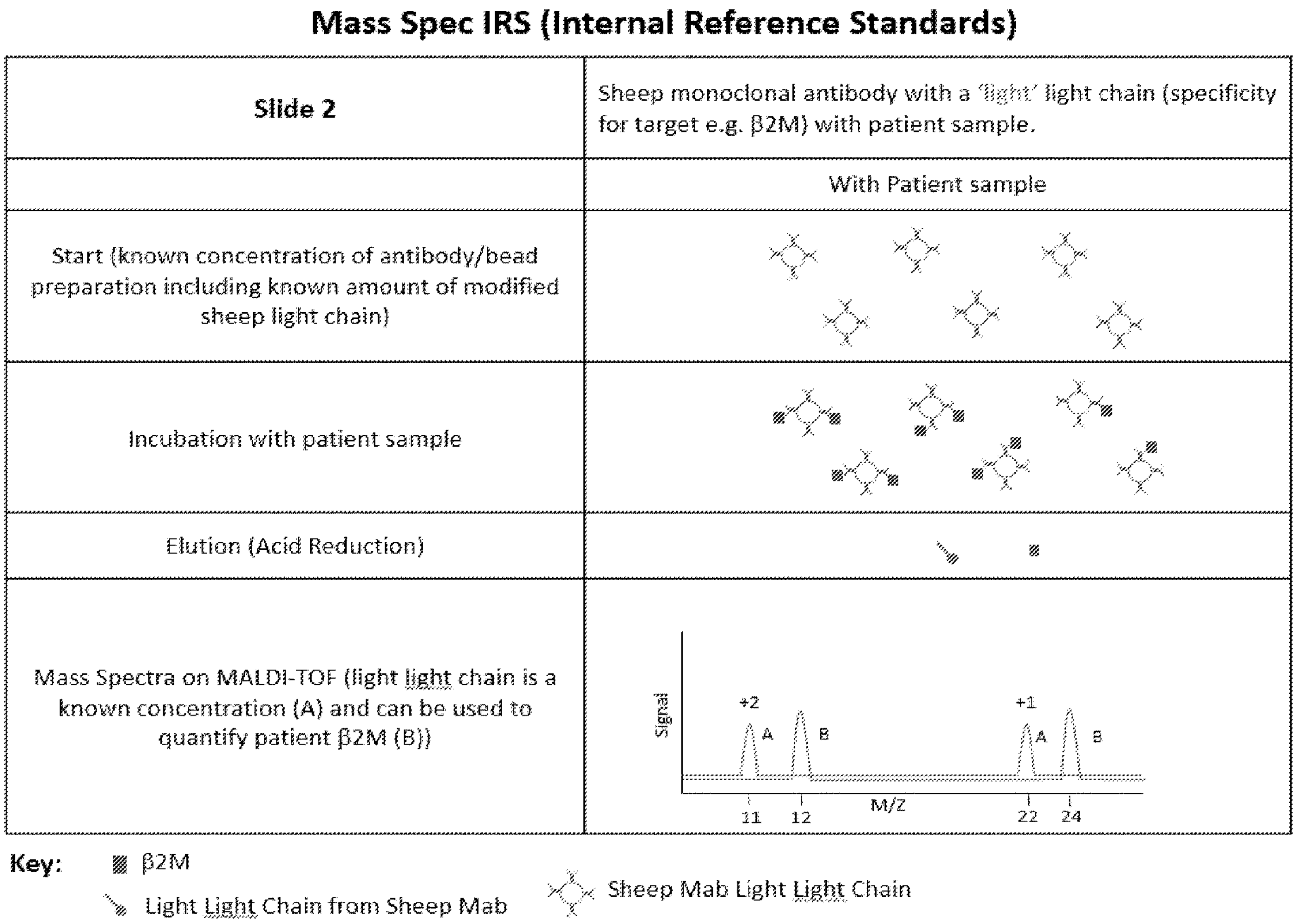
FIG. 2 shows use of the bound monoclonal antibody to detect a protein, such as β2M, on MALDI-TOF.

In FIG. 2, the antibody is incubated with a patient sample to bind to an analyte, such as β2M. After acid elution, the antibody and antigen are separated, and are detected using MALDI-TOF. In the example, the light chain is separated from the heavy chain and the light chain is detected and compared to the peak for the sample of the analyte. The amount of analyte may be corrected due to the known amount of light chain produced by acid elution in the absence of the antibody, which has been used to produce the predetermined calibration value.

FIG. 3 shows an example of a monoclonal antibody detecting a light chain from a patient sample. In this case the size of the monoclonal antibody is heavier that the light chain of the sample to be detected. This may be produced by either selecting the size of the light chain in the monoclonal antibody or alternatively making the monoclonal antibody heavier, for example by the addition of one or more additionally amino acids, for example, at the N or C terminus of the light chain residue of the monoclonal antibody. Techniques to produce such heavier monoclonal antibody light chains, or indeed monoclonal heavy chains should they be the peak being detected by MALDI-TOF, are generally known in the art.

Other control substances, such as those described above may also be used in a similar manner.

EXPERIMENTAL EXAMPLES

Background

Mass spectrometry (MS) allows the separation of analytes by mass-to-charge ratio (m/z). Polyclonal immunoglobulin light chains have a varied set of masses so typically produce a normally distributed bell-shaped curve of m/z against signal intensity. Monoclonal light chains resolve as a sharp peak extending out of the bell curve. We have previously observed that doubly charged (light chain ions ($[M+2H]^{2+}$) produce the best resolution by MALDI-TOF in the range m/z 10900 to 12300. The EXENT QIP-MS immunoassay pre-analytical phase exemplified has three main steps: (1) immunocapture of the analyte by magnetic beads, (2) simultaneous elution and reduction of the analyte, and (3) spotting of the analyte onto a MALDI-TOF target plate. We have chosen to include as an example a mass-modified protein standard attached to a magnetic bead that can be added during step 1 so that it is amalgamated with the analyte prior to step 2 and can be spotted simultaneously with it. This is important since this can used to control for variability in step 1 and subsequently to standardise or control the resultant analyte spectral signal obtained from the MALDI-TOF mass spectrometer.

Methods

Mass Modification of Immunoglobulins

Immunoglobulins were modified using biotin or biotinylated-PEG molecules via pentafluorophenyl-ester (PFP) or tetrafluorophenyl-ester (TFP) crosslinkers. These target both primary and secondary amines in proteins, and are more reactive and more stable than the more commonly used N-hydroxysuccinimide (NHS) ester group of crosslinkers. They have been shown to be suitable for biotin labelling of both proteins and amino acids and are available commercially (e.g. EZ-Link™ PFP-Biotin, cat no. 21218, Thermo Fisher Scientific, and Biotin-PEG36-PFP ester, cat no. BP-24318, BroadPharm). Immunoglobulins at 5 mg/ml in PBS were incubated with different amounts of PFP or TFP crosslinkers dissolved in DMSO, at room temperature on a shaker for various durations (hours to days). Reactions were quenched by the addition of glycine (1:1 molar) and then dialysed to remove unconjugated cross-linker.

Preparation of Mass Spec Standard Particle or Bead

To prepare the Mass Spec std bead, 10 μl of the modified immunoglobulin was diluted to 50 μl with PBS-tween and incubated with an anti-human IgG paramagnetic microparticle for 15 min. The beads were pelleted on a magnetic rack, the supernatant was removed, and the bead washed thrice with PBS-tween and once with water and stored until use.

EXENT QIP-MS Immunoassay

Serum samples or pure proteins were diluted and captured during the EXENT QIP-MS immunoassay using a paramagnetic microparticle containing antibodies specific for human immunoglobulin heavy and light chains (anti-IgG, IgA, IgM, total kappa and total lambda). These microparticles were conjugated to either stabilised sheep polyclonal antibodies or recombinant Camelid VH domain antibodies (Thermo Fisher Scientific). The beads were pelleted and washed sequentially with PBS-tween. The Mass Spec std particle bead was added to the mixture, pelleted and washed once with water. This was eluted with an acidic buffer solution containing both reducing agent and an ionisation control protein (see for example WO2021/019211). The elution was subsequently spotted, in a sandwich with MALDI matrix (α-Cyano-4-hydroxycinnamic acid) onto a MALDI-TOF target plate and dried. Mass spectra were acquired in positive ion mode on a Bruker Microflex MALDI-TOF-MS covering the m/z range of 5000 to 30,000 which includes the doubly charged ($[M+2H]^{2+}$, m/z 10900-12300) ions of the analyte (human kappa or lambda light chains), and those of the Mass Spec std.

Results

Mass Modification of Immunoglobulins

To produce a mass shifted molecule that can be used in the EXENT QIP-MS system, two parameters are required to be met; (1) a modification of the immunoglobulin light chain that does not interfere with the immuno-precipitation or immunocapture of the molecule and (2) to add (or indeed alternatively remove) mass that can be detected as an m/z shift. The addition of biotin using PFP crosslinking to the therapeutic monoclonal IgGK Daratumumab was used to show that modification of intact immunoglobulins with a corresponding mass shift in the m/z of the immunoglobulin light chain could be observed by MALDI-TOF (FIG. 4). FIG. 5 shows that this mass-shift due to biotinylation also works with polyclonal IgA and IgM samples. In all 3 cases the immunoprecipitation of these mass-modified proteins by camelid-antibody beads is unaffected. The mass increases seen with biotin alone are not sufficient to shift the masses beyond the expected biological range for +2 charge state ion; 10900 to 12300 Da; to achieve this, larger molecules are required. Biotin-PEG36-PFP was added to polyclonal IgA and IgM and the molecules captured by sheep anti-kappa light chain beads. A time course shows that a 4-hour reaction time is sufficient to modify the masses of the kappa light chains from a mean m/z of 11700 to 12650 (FIG. 6). This work was expanded using Biotin-PEG36-PFP modification of Daratumumab monoclonal protein (FIG. 7). A 6-hour 2-step addition of the modifying substance shifted nearly all the mass of the kappa light chain (FIG. 7*b*) compared to one with a single step of 2-hour duration (FIG. 7*a*). Biotin-PEG36-PFP could also be used to mass-shift the light chains on myeloma-derived monoclonal immunoglobulin, IgAK (FIG. 8*a*) and IgG2K (FIG. 8*b*). A similar mass-shifting of polyclonal immunoglobulin kappa light chains in human serum could be obtained using a related cross-linker (Biotin-PEG24-TFP) over 3 h or overnight (FIG. 9*ab*).

EXENT QIP-MS std

To illustrate the use of mass-modified immunoglobulins as in-situ MS controls, Daratumumab was labelled with Biotin-PEG36-PFP for 3 days. The resultant m/z of the light chain when analysed using the EXENT QIP-MS immunoassay using a sheep-anti-IgG bead suggested a single site had been modified (FIGS. 10 and 11). This single site modification was sufficient to increase the +2 m/z from 11700 to 12600 without effecting the ability of the IgGK immunoglobulin to be immuno-captured by the anti-IgG bead. A dilution series of this molecule over a 10-fold range showed that the concentration was positively associated with MS signal intensity (FIG. 11).

Spiking of the mass-modified Daratumumab bound to an anti-IgG bead into the EXENT QIP-MS immunoprecipitation IgA assay showed that simultaneous elution of the analyte and the mass modified molecule could be obtained. The mass-modified light chain +2 peak of the latter is clearly distinguishable from that obtained from a myeloma IgAL patient (FIG. 12) or the polyclonal IgA present in a healthy sample (FIG. 13).

The invention claimed is:

1. A method of immunopurifying and characterising an analyte from a sample comprising:

(i) providing a predetermined amount of a control substance bound to a first substrate via a linkage cleavable by acidic pH and/or reducing agents, wherein:
  - the control substance specifically binds the analyte; or
  - the control substance does not bind the analyte, and is combined with analyte-specific antibodies or fragments thereof bound to the first or a second substrate;

(ii) allowing the control substance or the analyte-specific antibodies or fragments thereof to bind to the analyte in the sample;

(iii) washing unbound material away from the first substrate and if present, the second substrate;

(iv) a) acid eluting the analyte from the control substance or the analyte-specific antibodies or fragments thereof; and
  b) cleaving at least a portion of the control substance from the first substrate by acidic pH and/or one or more reducing agents;

(v) performing mass spectrometry to identify two or more peaks, comprising at least one first peak associated with the presence of the analyte and at least one second peak associated with at least a portion of the control substance; and (vi) comparing the size or intensity of the at least one second peak to a predetermined calibration value to measure the analyte from the at least one first peak.

2. The method according to claim 1, wherein the control substance is a heteropolymer, which is a protein comprising two or more separable protein subunits, and the at least a portion of the control substance detected in the at least one second peak is at least a portion of one of the two or more separable protein subunits.

3. The method according to claim 2, wherein the control substance is an antibody or fragment thereof comprising at least one heavy chain or a fragment thereof and at least one light chain or a fragment thereof, and the at least one second peak is at least a portion of the light chain.

4. The method according to claim 1, wherein the predetermined calibration value is calculated by performing steps (i) to (v) without the analyte, and quantifying the at least a portion of the control substance.

5. The method according to claim 4, wherein the at least a portion of the control substance is quantified by liquid chromatography—mass spectrometry.

6. The method according to claim 1, wherein the at least a portion of the control substance detected in the at least one second peak are immunoglobulin light chains or fragments of light chains.

7. The method according to claim 1, wherein the mass of the at least a portion of the control substance is preselected to produce the at least one second peak separated from the at least one first peak when the mass spectrometry step (v) is performed.

8. The method according to claim 1, wherein the mass spectrometry is MALDI-TOF mass spectrometry, and the at least one first peak and the at least one second peak is m/z intensity.

9. The method according to claim 1, wherein the control substance and/or analyte-specific antibodies or fragments thereof are monoclonal antibodies or fragments thereof.

10. The method according to claim 9, wherein the analyte is an immunoglobulin or fragment thereof, and the control substance and/or monoclonal antibodies or fragments thereof have a different mass and/or charge when analysed by mass spectrometry.

11. The method according to claim 10, wherein the monoclonal antibodies or fragments thereof have had their mass modified to have a different mass to the immunoglobulin or fragment thereof.

12. The method according to claim 9, wherein the analyte-specific antibodies or fragments thereof are heavy chain class specific, light chain type specific, free light chain type specific, or heavy chain class-light chain type specific.

13. The method according to claim 1, wherein the first substrate comprises a predetermined amount of the control substance and a plurality of analyte-specific antibodies or fragments thereof.

14. The method according to claim 1, wherein the first and/or second substrate comprises a plurality of beads.

15. The method according to claim 1, comprising detecting, monitoring or prognosis of a disease by detecting the presence of an analyte according to claim 1, wherein the disease is B-cell related disease or other immune-related disease.

16. A kit for use in a method according to claim 1, comprising:
  - at least one substrate, comprising a predetermined amount of a control substance attached to the at least one substrate via linkage cleavable by acidic pH and/or reducing agents, wherein
  - i) the control substance is specific for the analyte, or
  - ii) the control substance is not specific for the analyte and the kit further comprises a plurality of analyte-specific antibodies, or fragments thereof; and a predetermined calibration value for the analyte.

17. The method according to claim 1, wherein the control substance bound to the first substrate is provided after contacting the analyte with the analyte-specific antibodies or fragments thereof.

18. The method according to claim 1, wherein the analyte is a serum protein.

19. The method according to claim 1, wherein the control substance and/or analyte-specific antibodies or fragments thereof are polyclonal antibodies or fragments thereof.

20. A method according to claim 12, wherein the control substance and/or the analyte-specific antibodies or fragments thereof are immunoglobulin heavy chain class specific, and the analyte is a lambda light chain or kappa light chain.

21. The method according to claim 1, wherein the analyte is an immunoglobulin or fragment thereof.

22. The method of claim 21, wherein the analyte is selected from human IgG, IgA, IgM, IgD or IgE, lambda light chain or kappa light chain.

* * * * *